United States Patent [19]
Makovec et al.

[11] 3,985,878
[45] Oct. 12, 1976

[54] ANTI-INFLAMMATORY AND ANTIRHEUMATIC COMPOUNDS AND PREPARATION

[75] Inventors: Francesco Makovec, Taccona (Milan); Paolo Senin, Monza (Milan); Luigi Rovati, San Fruttuoso di Monza (Milan), all of Italy

[73] Assignee: Rotta Research Laboratorium S.p.A., S. Fruttuoso di Monza (Milan), Italy

[22] Filed: July 10, 1975

[21] Appl. No.: 594,914

[30] Foreign Application Priority Data
Aug. 12, 1974  Italy .................................. 69523/74

[52] U.S. Cl. ............................ 424/250; 260/268 BC
[51] Int. Cl.² ........................................ C07D 403/12
[58] Field of Search ............... 260/268 BC; 424/250

Primary Examiner—Nicholas S. Rizzo
Assistant Examiner—Jose Tovar
Attorney, Agent, or Firm—Sughrue, Rothwell, Mion, Zinn and Macpeak

[57] ABSTRACT

Anti-inflammatory antirheumatic compounds of the formula:

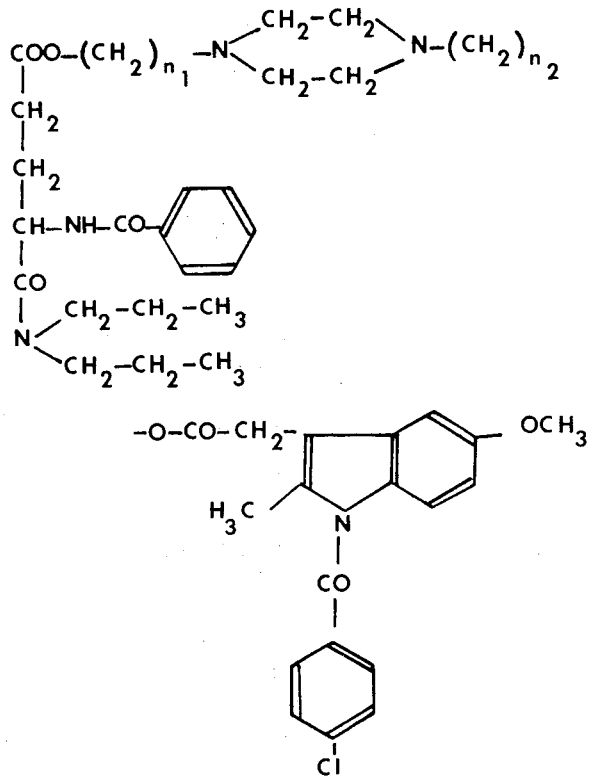

wherein $n_1$ and $n_2$ are each either 2 or 3, and wherein the two tertiary amino-groups may, if desired, be present in the form salified by a pharmaceutically acceptable acid such as oxalic, citric, maleic, fumaric or hydrochloric acid. The preferred compound is N'-2-[1-(p-chlorobenzoyl)-5-methoxy-2-methyl-3-indoleacetoxy]-ethyl-N-3-(N-benzoyl-N',N'-di-n-propyl-DL-isoglutaminoyl)-oxypropyl-piperazine, preferably in the form of dimaleate.

10 Claims, No Drawings

ANTI-INFLAMMATORY AND ANTIRHEUMATIC COMPOUNDS AND PREPARATION

This invention relates to compounds having a therapeutically useful anti-inflammatory and antirheumatic activity, and to pharmaceutical preparations based on said compounds.

Known anti-inflammatory compounds are typically used upon acute forms of inflammation which are characterized by intumescence and a reddening of the affected region of the body. Since these forms are particularly painful, some anti-inflammatory compounds additionally exhibit an analgesic activity.

Difficulties are experienced, however, in cases involving a progressive lesion of cartilage and bone (arthrosis) rather than mere reddening and intumescence. In fact, all known anti-inflammatory compounds exert an inhibiting action on both the cartilage and bone matrix, so that their continuous use in chronic forms of disease enhances arthrosis and induces osteoporosis. Moreover, known anti-inflammatory compounds adversely affect the gastric mucosa and may even produce gastric ulcer and perforation; their administration to subjects suffering from gastroduodenitis and ulcers is therefore impossible or, at least, extremely dangerous.

An object of this invention is to provide thereapeutically valuable anti-inflammatory compounds having the following properties:

1. high activity against acute inflammatory forms;
2. satisfactory analgesic activity;
3. high activity against chronic osteoarthritic forms (arthrosis),
4. absence of irritative and ulcerative effects upon gastric mucosa.

Accordingly, the invention provides novel anti-inflammatory and antirheumatic compounds having the formula (A) hereinbelow:

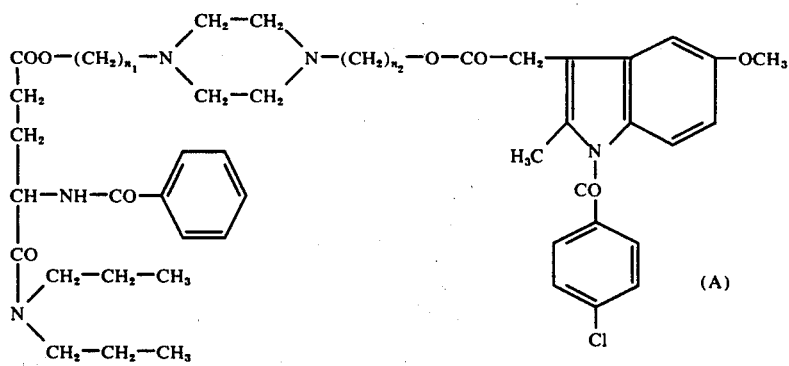

(A)

wherein $n_1$ and $n_2$ are each integers, either 2 or 3, and wherein the two tertiary amino-groups may, if desired, be present in the form salified by a pharmaceutically acceptable acid, such as oxalic, citric, maleic, fumaric or hydrochloric acid.

Compounds (A) may be prepared by either of the two following processes:

Process a:

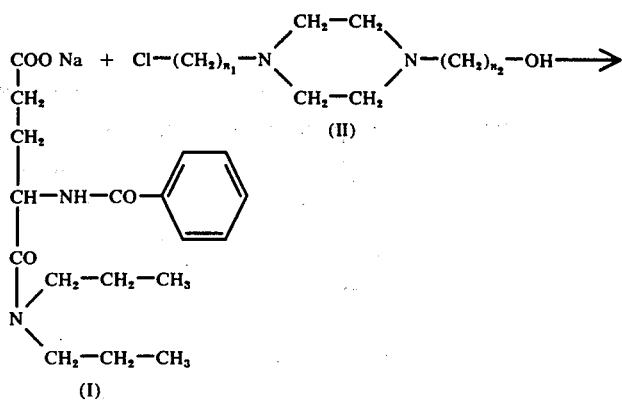

(I)

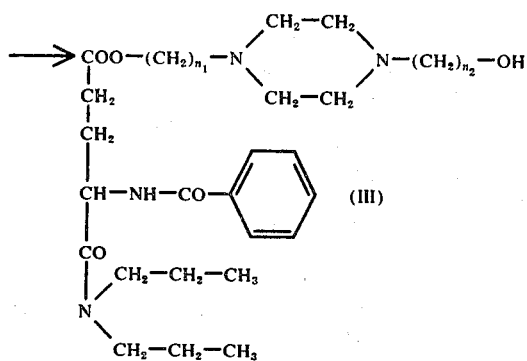
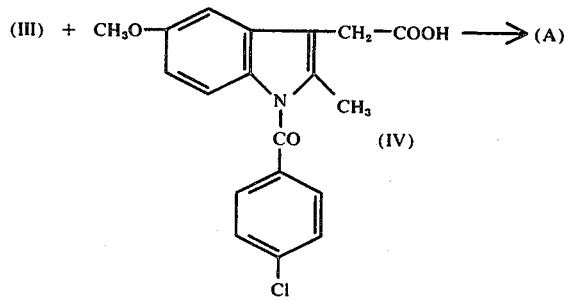
Process "b":
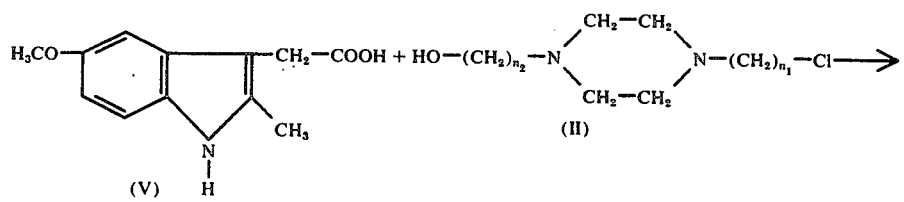
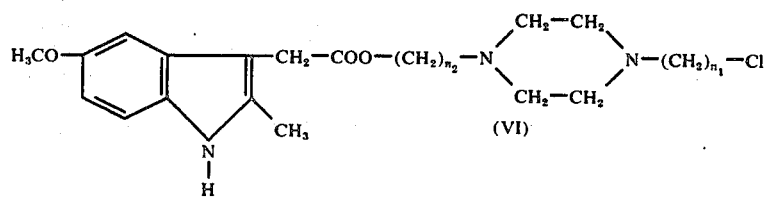
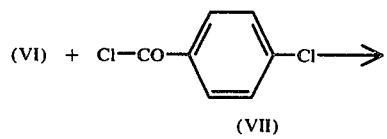
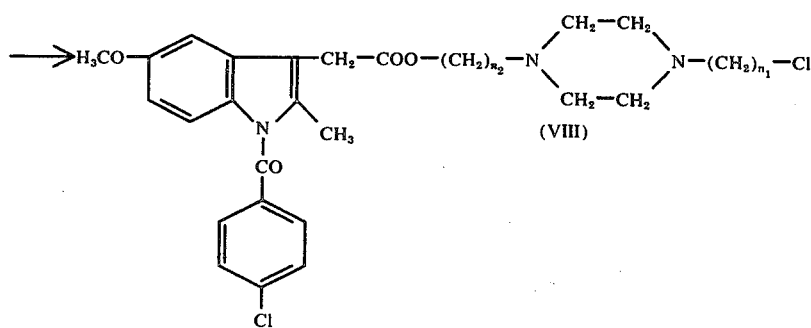

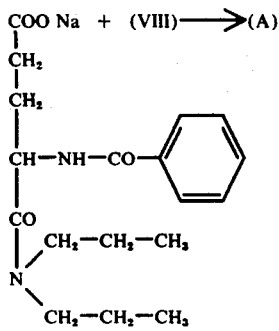

COO Na + (VIII) ⟶ (A)

In Process a, N-benzoyl-N', N'-di-n-propyl-DL-isoglutamine is reacted, in a solvent such as sulfolane, toluene, xylene or dimethylsulphoxide, with an N-(hydroxyalkyl)-N'(chloro-alkyl)-piperazine in the presence of sodium bicarbonate, at a temperature from 70° to 150° C, preferably 110° C, for a period of between 2 and 12 hours. The intermediate product so obtained, consisting of N'-(2 or 3)-hydroxyalkyl-N-(2 or 3)-(N-benzoyl-N',N'-di-n-propyl-DL-isoglutaminoyl)-oxyalkyl-piperazine is reacted with 1-(p-chlorobenzoyl)-5-methoxy-2-methyl-3-indoleacetic acid in the presence of a condensation agent, such as N,N'-dicyclohexylcarbodiimide or N,N'-carbonyl-diimidazole, in a solvent such as tetrahydrofuran, dioxane, chloroform, ethyl acetate or acetone, for a period from 8 to 48 hours, at a temperature from 10° C to 30° C, thereby yielding the compound (A).

In Process b, 5-methoxy-2-methyl-3-indolyl-acetic acid is reacted with N-(hydroxyalkyl)-N'-(chloroalkyl)-piperazine in the presence of a condensation agent such as N,N'-dicyclohexylcarbodiimide or N,N'-carbonyl-diimidazole, in a solvent such as tetrahydrofuran, dioxane, chloroform, ethyl acetate or acetone, for between 8 and 48 hours, at a temperature from 10° to 30° C. The resulting N'-(2 or 3)-chloroalkyl-N-(2 or 3)-(5-methoxy-2-methyl-3-indoleacetoxy)-alkyl-piperazine is reacted with a suspension of sodium metal, sodium iodide or sodium phenate in a solvent such as benzene or toluene, for between 2 and 8 hours at a temperature from 10° to 40° C. Subsequently, without isolating the organo-metallic intermediate, the reaction mass is admixed at 5°–10° C with a stoichiometric amount of p-chlorobenzoyl chloride and the reaction is allowed to proceed for from 4 to 12 hours at a temperature from 10° to 40° C. A corresponding N'-(2 or 3)-chloroalkyl-N-(2 or 3)-[1-(p-chlorobenzoyl)-5-methoxy-2-methyl-3-indoleacetoxy]-alkylpiperazine is obtained, which is reacted with N-benzoyl-N',N'-di-n-propyl-D,L-isoglutamine, in a solvent such as toluene, xylene, sulfolane, or dimethylsulphoxide, in the presence of a stoichiometric amount of sodium bicarbonate, at a temperature between 60° and 120° C for 2 to 12 hours, thereby yielding the compound (A).

The compound (A) is salifiable in a manner known per se, as will be seen in the specific Examples hereinafter.

The preferred compound, hereinafter termed "CR 604", is N'-2-[1-(p-chlorobenzoyl)-5-methoxy-2-methyl-3-indoleacetoxy]ethyl-N-3-(N-benzoyl-N',N'-di-n-propyl-DL-isoglutaminoyl)oxypropyl-piperazine, preferably in the form of dimaleate.

EXAMPLE 1

N'(2-hydroxy-ethyl)-N-3(N-benzoyl-N',N'-di-n-propyl-DL-isoglutaminoyl)-oxy-propyl piperazine.

To a solution of 33.4g (0.1 moles) of N-benzoyl-N', N-di-n-propyl-D,L-isoglutamine in 200 cc of dimethylsulphoxide there are added in sequence, under agitation, 5.4g (0.1 moles) of sodium methylate, and 10.6 g (0.1 moles) of N-3-chloropropyl-N'-2 hydroxyethyl piperazine. The temperature is brought to 105° and it is left under agitation for 12 hours at this temperature. The solvent is vacuum-evaporated, and the residue recovered with ethyl acetate, extracted with a dilute solution of hydrochloric acid; the aqueous acid phase is alkalynised to pH 10 with a 4N solution of sodium hydroxide and re-extracted twice in succession with ethyl acetate. The combined organic phase are anhydrified with anhydrous sodium sulphate, filtered and dried. The oily residue thus obtained is dissolved in 150cc of methanol; by the addition of a methanolic solution of oxalic acid the di-oxalate is precipitated. Yield 81%. m.p. 181°–184°.

EXAMPLE 2

N'-2-[1-(p-chlorobenzoyl)-5-methoxy-2-methyl-3-indoleacetoxy]ethyl-N-3-(N-benzoyl-N', N'-di-n-propyl-DL-isoglutaminoyl)-oxypropyl-piperazine (CR 604).

To a titrated solution of 400 cc of ethyl acetate containing 0.1 moles of N'-(2-hydroxy-ethyl)-N-3-(N-benzoyl-N',N'-di-n-propyl-DL-isoglutaminoyl)oxypropyl piperazine [obtained by dissolving 71.9 g (0.105 moles) of the corresponding di-oxalate in 500 cc of water, bringing this solution to a pH of between 9 and 10 with sodium bicarbonate and finally extracting the oily emulsion thus formed, twice in succession with a total of 400 cc of ethyl acetate], there are added successively 35.8 g (0.1 moles) of 1-(p-chloro-benzoyl)-5-methoxy-2-methyl-3-indoleacetic acid and 20.6 g (0.1 moles) of N, N'-dicyclohexylcarbodiimide; this is left at room temperature for 24 hours, and after having filtered the N',N'-dicyclohexyl urea precipitate the organic phase is then washed with dilute HCl, a solution of sodium bicarbonate and a saturated solution of sodium chloride. The ethyl acetate is dried with anhydrous sodium sulphate, filtered and dried off. The oily residue is dissolved in 600 cc of methanol; the di-oxalate is precipitated by the addition of a solution of oxalic acid in methanol. Yield 85% m.p. 190°–192° (crystallised by methanol). Microcrystalline substance, creamy white colour, slightly soluble in ethanol, methanol, acetone. Insoluble in $H_2O$. Microanalysis (CR 604 dioxalate):

|  | C% | H% | N% |
|---|---|---|---|
| calc: | 58.60 | 6.10 | 6.83 |
| found: | 59.01 | 6.19 | 6.79 |

By the same method one can obtain the di-maleate. Yield 83%. m.p. 146°–148° C (crystallised by ethanol). Microcrystalline pale cream coloured substance; slightly soluble in ethanol, acetone; more soluble in methanol. Insoluble in water.

Alternatively, still with the same procedure, but less advantageously, one can obtain the di-hydrochloride. Yield 70%. m.p. 107–111 (with dec.).

Substance of amorphous appearance, slightly yellow in colour. Soluble in methanol and ethanol. Fairly soluble in acetone. Hardly soluble in water (solubility about 0.5% at 25°).

EXAMPLE 3

N'-3-(chloro-propyl)-N-2-(5-methoxy-2-methyl-3-indoleacetoxy)-ethyl-piperazine.

To a solution of 21.9 g (0.1 moles) of 5-metoxy-2-methyl-3-indolyl acetic acid, in 300 cc of ethyl acetate there are added successively 20.6 g (0.1 moles) of N-(2-hydroxy-ethyl)-N'-3-(chloro-propyl)-piperazine and 20.6 g (0.1 moles) of N,N'-dicyclohexylcarbodiimide; this is left under agitation at room temperature for 24 hours, and after filtering off the N,N'-dicyclohexylurea precipitate the organic phase is then washed in a solution of sodium bicarbonate and a saturated solution of sodium chloride.

The ethyl acetate is dried with anhydrous sodium sulphate, filtered and dried off. The oily residue is used, as it is, in the next stage. Yield 80%.

EXAMPLE 4

N'-3-(chloro-propyl)-N-2-[1-(p-chlorobenzoyl)-5-methoxy-2-methyl-3-indoleacetoxy]-ethyl-piperazine.

To a solution of 40.8 g (0.1 moles) of the oil, prepared according to the description of Example 3, in 400 cc of toluene, there are added under a nitrogen current 12g of sodium iodide (0.1 moles) in a suspension of 20% in vaseline oil; this is left to react under good agitation, at room temperature for 6 hours, it is then cooled to 0° C and 17.5g (0.1 moles) of p-chlorobenzoyl chloride are added. Then the temperature is raised to room temperature and it is again left to react for at least 6 hours.

The organic phase is washed in an aqueous solution of sodium bicarbonate and then with water; it is anhydrified with anhydrous sodium sulphate, filtered and dried by evaporation under vacuum. The oily residue thus obtained is dissolved in 200 cc of methanol; by the addition of a methanolic solution of oxalic acid the di-oxalate is precipitated. Yield 68%. m.p. 207°–210° (with dec.).

EXAMPLE 5

N'-2[-1(p-chloro benzoyl)-5-methoxy-2-methyl-3-indoleacetoxy]-ethyl-N-3-(N-benzoyl-N',N'-di-n-propyl-D,L-isoglutaminoyl)-oxypropyl-piperazine (CR 604 see Example 2).

To a suspension of 33.4g (0.1 moles) of N-benzoyl-N',N'-di-n-propyl-D,L-isoglutamine in 300 cc of anhydrous toluene there are added, under agitation, 5.4g (0.1 moles) of sodium methylate; the temperature is brought up to 60° and it is left in agitation for 3 hours; at this point there are added 400 cc of a toluene solution containing 0.1 moles of N'-3-(chloropropyl)-N-2-[-1-(p-chlorobenzoyl)-5-methoxy-2-methyl-3-indoleacetoxy]-ethyl-piperazine (obtained by dissolving 76.2g (0.105 moles) of the corresponding di-oxalate in 600 cc of water, bringing the said solution to a pH between 9 and 10 with sodium carbonate, and finally extracting the oily emulsion thus formed, twice in succession, with a total of 400 cc of toluene).

The temperature is raised to 100° C and it is left to react for 12 hours; next, the organic phase is washed with an aqueous solution of hydrochloric acid, of sodium bicarbonate and finally of sodium chloride. It is anhydrified with anhydrous sodium sulphate, then filtered, and dried by evaporation in vacuum.

The oily residue thus obtained is dissolved in 600 cc of methanol; the maleate is precipitated by the addition of a solution of maleic acid in methanol.

Yield 80%.

EXAMPLE 6

N'-(3-hydroxy-propyl)-N-3-(N-benzoyl-N',N'-di-n-propyl-DL-isoglutaminoyl)-oxypropyl-piperazine.

Procedure as in Example 1, using 22.0 g (0.1 moles) of N-3-chloropropyl-N'-3-hydroxypropylpiperazine instead of N-3-chloropropyl-N'-hydroxyethylpiperazine.

Yield 74%. m.p.: 173°–176°. (di-oxalate).

EXAMPLE 7

N'-3-[1(p-chlorobenzoyl)-5-methoxy-2-methyl-3-indoleacetoxy]-propyl-N-3-(N-benzoyl-N',N'-di-n-propyl-DL-isoglutaminoyl)-oxypropyl-piperazine. (CR 613).

Procedure as as in Example 2, using 51.8g (0.1 moles) of N'-(3-hydroxy-propyl)-N-3-(N-benzoyl-N',-N'-di-n-propyl-DL-isoglutaminoyl)-oxypropyl-piperazine in place of N'-2-(hydroxyethyl)-N-3-(N-benzoyl-N',N'-di-n-propyl-DL-isoylutaminoyl)-oxypropyl-piperazine.

Yield 80%, m.p. 138–141(di-maleate). Microcrystalline substance, creamy yellow in colour; slightly soluble in ethanol, acetone; more soluble in methanol. Insoluble in water. Microanalysis (CR 613-di-maleate):

|  | C% | H% | N% |
|---|---|---|---|
| calc. | 60.56 | 6.28 | 6.42 |
| found. | 60.31 | 6.41 | 6.28 |

EXAMPLE 8

N'-(2-hydroxy-ethyl)-N-2-(N-benzoyl-N',N'-di-n-propyl-DL-isoglutaminoyl)-oxyethyl-piperazine.

Procedure is as in Example 1, using 19.3 g (0.1 moles) of N-2-chloro-ethyl-N'-2-hydroxyethyl-piperazine in place of N-(2-hydroxy-ethyl)-N'-3-(chloro-propyl)-piperazine. Yield 78%. m.p. 187°–190°(di-oxalate).

EXAMPLE 9

N'-2-[1-(p-chlorobenzoyl)-5-methoxy-2-methyl-3-indoleacetoxy]-ethyl-N-2-(N-benzoyl-N',N'-di-n-propyl-D,L-isoglutaminoyl)-oxyethyl-piperazine (CR 626).

Procedure is as in Example 2 using 49.2g (0.1 moles) (analytical calculation) of N'-2-(hydroxy-ethyl)-N-2-(N-benzoyl-N',N'-di-n-propyl-D,L-isoglutaminoyl)-oxyethyl piperazine in place of N'-2-(hydroxyethyl-N-3-(N-benzoyl-N',N'-di-n-propyl-DL-isoglutaminoyl)-oxypropyl-piperazine. Yield 77%. m.p. 163°–164° C (di-maleate). Microcrystalline substance, creamy yellow in colour; slightly soluble in ethanol, acetone; more soluble in methanol. Insoluble in water, Microanalysis (CR 626-di-maleate)

|  | C% | H% | N% |
|---|---|---|---|
| calc. | 59.90 | 6.07 | 6.59 |
| found | 59.17 | 5.91 | 6.47 |

The pharmacological characteristics of the compounds which are the object of this invention will now be described in the order shown at the beginning, i.e. describing their activity in acute inflammatory forms, their analgesic activity, their antiarthrosis activity, and the absence of any ulcerative activity or activity in any way irritative upon gastric mucosa, The experiments reported were performed either on animals or human beings.

Experiments on animals

1a. Anti-inflammatory activity: this activity was measured by the paw test according to Doemnjoz, characterised in its carrying out by the following method:

To young rats of medium weight of 200 g there is administered by hypodermic injection into the right paw an aqueous suspension of carragheen at 1%, 1 hour after the oral administration of the drugs under investigation.

After two hours from the administration of the carragheen, the pawas are disjointed, weighed, and comparison is made between the injected paw, meanwhile swollen, and the paw not interfered with.

The difference in weight is the greater in proportion as the anti-inflammatory is more active. Evaluation is made by calculating the $ED_{50}$ in mg/kg by oral means, i.e., the drug dose capable of reducing by 50% the inflammation of the treated paw compared with the not treated paws.

On Table 1 there are shown and compared exactly the $ED_{50}$ of the compounds which are the objects of this invention, and of a few of the better known anti-inflammatories. This evaluation is expressed both in mg/kg of animal weight and in micromoles/Kg of weight of the animal. This second evaluation, more reliable because taken with reference to each single molecule, shows that among all the compounds studied the most interesting is that marked by the initials CR 604.

TABLE 1

| Acute anti-inflammatory activity (Domenjoz test) | | |
|---|---|---|
| | Molecular weight | $ED_{50}\mu m/Kg$ per os (*) | $ED_{50}$ mg/kg per os |
| CR 604 (di-maleate) | 1076.63 | 11.5 | 12.3 |
| CR 613 (di-maleate) | 1090.70 | 13.6 | 14.9 |
| CR 626 (di-maleate) | 1062.60 | 15.0 | 16.0 |
| Phenylbutazone | 308.37 | 463.7 | 143 |
| Acetylsalicylic ac. | 180.15 | 1254.5 | 226 |
| Mephenamic ac. | 241.30 | 439.4 | 106 |
| Ibuprofen | 206.27 | 436.3 | 90 |
| Indometacin | 357.81 | 17.3 | 6.2 |

(*) micromoles/Kg.

1b. Pellets-induced granuloma test:

Another important test for the evaluation of an anti-inflammatory is that of cotton pellets. This consists of planting a sterile cotton pellet under the rat's back skin.

This pellet is left in situ for a week while the animals are treated daily with various doses of the drug being examined. Evaluation is effected by weighing the pellets taken at the given time and dried, comparing the weight of those of the treated animals with the checks. Thus the $ED_{50}$ is expressed as a drug dose capable of reducing by 50% the increase in weight which the pellet undergoes through infiltration of the surrounding inflamed tissue.

In Table 2 there are shown the results confined to the CR 604 and to Indometacin. In this test also, the CR 604, one of the compounds of this invention, shows a high anti-inflammatory activity.

TABLE 2

| Acute anti-inflammatory activity (granuloma test) | | |
|---|---|---|
| SUBSTANCES | Molecular weight | $ED_{50}\mu m/kg$ per os (*) | $ED_{50}$ mg/kg per os |
| CR 604 (di-maleate) | 1076.63 | 25.6 | 27.6 |
| Indometacin | 357.81 | 23.5 | 8.41 |

(*) micromoles/kg

2. Analgesic activity: The analgesic activity of an anti-inflammatory can be examined traditionally by the phenylquinone method based on the fact that intraperitoneal administration to a rat of an irritant substance such as phenylquinone induces vocal reactions ("squirring") in the animal.

From the number of these reactions one judges the pain sensitivity. Evaluation is effected as $ED_{50}$ in mg/kg of animal weight, and that is the dose which reduces by 50% the response to the irritative stimulus.

The results set out in Table 3, especially those referring to the micromoles, make evident, especially if compared to the values relative to indometacin, an analgesic activity of CR 604 which is even more interesting.

TABLE 3

| Analgesic activity in the rat. Phenylquinone test, x os Sum. | | |
|---|---|---|
| SUBSTANCES | Molecular weight | $ED_{50}\mu m/kg$ per os (*) | $ED_{50}$ mg/kg per os |
| CR 604 (di-maleate) | 1076.63 | 5.3 | 5.72 |
| Indometacin | 357.81 | 5.6 | 2 |
| Phenylbutazone | 308.37 | 324.0 | 100 |

(*) micromoles/kg

3. Activity in chronic osteoarthritic forms: Experimental evaluation of the compounds being examined for their activity on osteoarthrosic forms was divided into two parts: in vitro and in vivo.

These tests consist mainly of the evaluation of the possibilities for the drugs of positively influencing reconstruction of the osteocartilaginous tissue around the joint, since generally these diseases are characterised by destruction of these tissues which starts from the proteic stroma and spreads through to the mineral part in the case of bones.

a. Tests in vitro: These tests consist of the cultivation in vitro, i.e., outside the organism, of tissue of the same embriological origin in relation to the osteoarticular. Upon the growth of this tissue there is then measured the activities of the various drugs. The units of measurement of these activities is the production of glucosaminoglicanes (mucopolysaccharides measured by the turbidimetric method).

A series of tests of this type which have already been published [see for example Karzel et altri - Exerpta Medica int. Congr. series no. 188 (1968, p.102)] reveals that all previously known anti-inflammatories cause a reduction in the activity of these tissues and this explains the damage which can be observed in a human being after prolonged use of such drugs.

The compounds which form the subject of this invention were evaluated according to this test and compared with known anti-inflammatories.

The results are recorded in Table 4.

TABLE 4

Activity of the compounds upon the production of mucopolysaccharides from fibroblast culture in vitro (*)

| SUBSTANCES | DOSES: µg/ml of culture liquid | Mucopolysaccharide products at the tenth day of incubation. Values expressed in % related to the checks |
|---|---|---|
| INDOMETACIN | 2 | 78 |
| PHENYLBUTAZONE | 10 | 58 |
| MEFENAMIC ACID | 10 | 58 |
| CR 604 (DI-MALEATE) | 6 | 108 |

(*) Mucopolysaccharides measured by the turbidimetric method. Karzel et al. Excerpta Medica - Med. Int. Congr. Series no. 188 (1968), p. 102

Examination of Table 4 shows that CR 604 is the unique compound which does not harm, in this in vitro culture of collagen tissue, the growth and the production of mucopolysaccharides.

B. Tests in vivo: Osteolathyrism in the rabbit.

Osteolathrism consists of inducing into young rabbits a dystrophy of the bone joint system, administering every day aminoacetonitrile by i.p. means, in the quantity of 100 mg/kg of body weight. With this treatment, in about 30 days, the following changes are shown in the rabbit:

Loss of weight (related to the checks physiologically treated), ptosis of the auricular pavilion, loss of fur, deformation of the front and rear limbs, deterioration of the general condition.

All this takes place because the aminoacetonitrile is a collagen tissue poison which changes the biochemical composition of the joint cartilages and the bones.

An evaluation of the therapeutic activity can be made either by biochemical evaluation, i.e. by measuring the quantity of aminosugars in these tissues, or by considering only the general symptoms, which are proportional to the diminution of the aminosugars.

In Table 5 this latter evaluation is reported, in which every symptom was evaluated by allotting it a number from 0 to 4, 4 indicating the maximum amount of damage and 0 indicating no damage.

On Table 5 there are given the results of treatment evaluated on the 25th day, comparing the groups treated only with a physiological solution, only with aminoacetonitrile, with aminoacetonitrile and CR 604, with aminoacetonitrile and Indometacin in the prescribed doses.

Each group consisted of 8 animals.

The results obtained show that aminoacetonitrile produces very high symptomatologic, with great aggravation of the indicated symptoms. Indometacin alone cannot prevent the occurrence of these conditions which are, on the other hand, well countered by CR 604, which greatly modifies these toxic symptoms.

4. Irritant and ulceroid activity on the gastric mucosa

The experimental evaluation of this activity was made on rats, by the method here reported:

The compound is administered orally to rats which have fasted for 12 hours, the animals being killed 4 hours after the administration.

Regarded as positive, i.e. with stomach damage, are those animals which have at least one haemorrhage point on the stomach wall.

By $ED_{50}$ there is meant that dose of the drug which can prevent in 50% of the animals treated, the formation of these haemorrhages.

In Table 6 there are compared CR 604 and Indometacin, since the latter is, amongst them all, the nearest to the anti-inflammatory activity values of CR 604.

The results obtained show that, whereas the gastrolesive dose of Indometacin is very low, even if expressed in micromoles, that of CR 604 is so high as to be of no practical importance, being roughly equal to a fatal dose.

TABLE 6

Gastrolesive activity in rats: $ED_{50}$ gastrolesive

| SUBSTANCE | Method of administ. | Molecular weight | $ED_{50}$ gastrol. in µm/kg (*) | $ED_{50}$ gastrol. in mg/kg |
|---|---|---|---|---|
| Indometacin | Oral | 357.81 | 33.5 | 12 |
| CR 604 (di-maleate) | Oral | 1076.63 | 330.1 | 355.2 |
| CR 613 (di-maleate) | Oral | 1090.70 | 277.4 | 302.6 |
| CR 626 (di-maleate) | Oral | 1062.60 | 341.7 | 363.1 |

(*) micromoles/kg

TOLERANCE IN ANIMALS

For these substances, and particularly for CR 604, tolerance tests were made, subacute and chronic, by up to 6 months administration to the animals. Results show that the product, even in quantities greater than

TABLE 5

30–35 days old rabbits treated with aminoacetonitrile Drugs administered per i.p. means

| SUBSTANCES | Days of treatm. | Ptosis of auricular pavilion | Loss of fur | General Condition of Animal | Deformed gait of back legs | Deformed gait of front legs | Loss of weight |
|---|---|---|---|---|---|---|---|
| Physiological checks | 25 | 0 | 0 | 0 | 0 | 0 | 0 |
| Aminoacetonitrile checks 100 mg/kg/day | 25 | 1.2 | 3 | 3.2 | 2.3 | 2.8 | 3.8 |
| CR 604 (di-maleate) 15 mg/kg/day + amino acetonitrile 100 mg/kg/day | 25 | 0.2 | 0 | 0.2 | 0.6 | 0 | 0 |
| Indometacin 5 mg/kg/day + Aminoacetonitrile 100 mg/kg/day | 25 | 1.4 | 3 | 3.8 | 1.6 | 3.2 | 3.5 | those recommended for human beings are well tolerated without any special anatomical or functional lesion.

THERAPEUTIC USE IN HUMAN BEINGS

The compounds which are the object of this invention can be administered to humans by oral means in the form of tablets and capsules containing quantities of the substance varying between 50 and 150 milligrammes.

For example, for CR 604 (di-maleate), capsules for oral use can be prepared containing 75 mg of compound thoroughly mixed with a pharmaceutically acceptable excipient, such as, for example: starch, lactose, talc, magnesium stearate, etc.

The minimum recommended dose is 3 capsules per day, which may be doubled in cases requiring it.

Suppositories can also be prepared containing 100–200 mg of CR 604 (di-maleate) dispersed in a pharmaceutically acceptable excipient.

b. The uropepsinogene calculation makes it apparent that whereas in the subjects treated with CR 604 this substance diminishes in the urine, it increases on the other hand in the subjects treated with Indometacin. This test demonstrates objectively what was stated above, in that the uropepsinogene shows the quantity of pepsin secreted in the stomach and eliminated through the urine.

Gastric secretion of pepsin is increased by agents which irritate and damage the gastric mucosa.

c. In the subjects treated with CR 604 there is a reduction in the excretion of urinary calcium, whereas in the subjects treated with Indometacin there is a tendency to an increase. Excretion of calcium is related to the destruction of the fibrils of the proteic bone matrix which thus also loses the calcium deposited upon it.

The administration of known anti-inflammatories brings about the lysis of these fibrils with loss of calcium. On the contrary CR 604 does not induce this destruction or reduces it.

TABLE 7

| SUBSTANCES | Epigastric pain (expressed as % of patients in pain) | | | Uropepsinogene (expressed in equivalent mg of tyrosine per day) | | | Urinary calcium (in mg/1000 cc of urine) | | |
|---|---|---|---|---|---|---|---|---|---|
| | Before treatment | After one week | After 3 weeks | Before treatment | After one week | After three weeks | Before treatment | After one week | After three weeks |
| CR 604 (di-maleate) | 0 | 3.3 | 0 | 216.3 | 209.8 | 153.8 | 132 | 107 | 98 |
| INDOMETACIN | 0 | 46.6 | 53.3 | 164.7 | 208.1 | 345.7 | 126 | 137 | 148 |

From 1 to 3 of these suppositories may be administered per day, as required.

Obviously other forms can be prepared which can be administered by oral or rectal means, with excipients acceptable from the pharmacological point of view.

The desired therapeutic effects of these products, and particularly CR 604, can also be demonstrated in human beings, following the more scientifically advisable methods, such as the double-blind technique.

Thus for example comparing CR 604 administered in capsules of 75 mg (6 per day), with Indometacin in capsules of 25 mg (6 per day), i.e. in approximately equimolecular doses on a group of 60 subjects treated (30 with CR 604 and 30 with Indometacin), one notes that (see Table 7):

a. Whereas Indometacin in 46.6% of the subjects treated (after 1 week of treatment) and in 53.3% of the subjects treated (after 3 weeks of treatment) induces gastric disturbances such that in some cases cessation of the therapy is advisable, CR604 does not induce any appreciable disturbance with therapeutically equiactive doses.

Thus for the compound CR 604, also in human beings, we meet with the same characteristics as those precisely specified in the in vitro tests and the tests on animals.

These characteristics amply justify a therapeutic innovation of considerable importance.

What is claimed is:

1. An anti-inflammatory antiarthrosic compound having the formula:

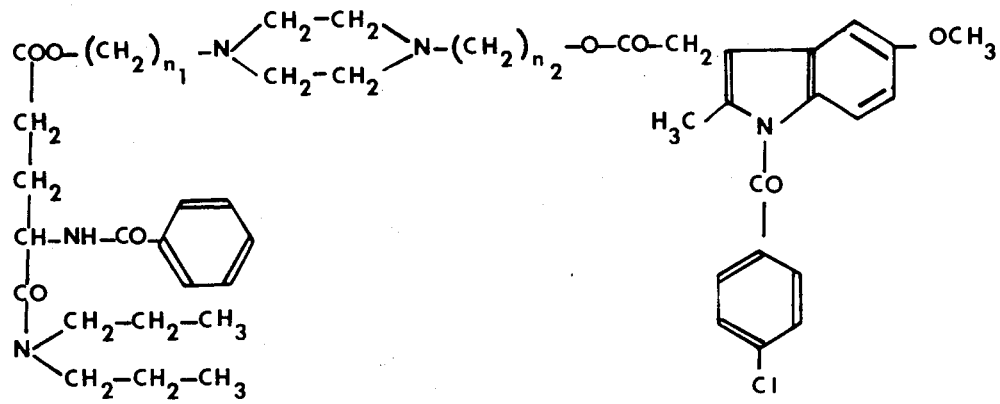

wherein $n_1$ and $n_2$ are integers, either 2 or 3, or a salt thereof with a pharmaceutically acceptable acid.

2. A compound as in claim 1, in which the two tertiary amino groups of the piperazine moiety are salified by oxalic, citric, maleic, fumaric or hydrochloric acid.

3. A compound as in claim 1 consisting of N'-2-[1-(p-chlorobenzoyl)-5-methoxy-2-methyl-3-indoleacetoxy]-ethyl-N-3-(N-benzoyl-N',N'-di-n-propyl-DL-isoglutaminoyl)-oxypropyl-piperazine.

4. A compound as in claim 3 in which the two tertiary amino groups of the piperazine moiety are salified by maleic acid.

5. An anti-inflammatory, anti-rheumatic composition consisting essentialy of a compound or salt of claim 1 and a pharmaceutically acceptable excipient.

6. The composition of claim 5, wherein said compound is N'-2-[1-(p-chloro-benzoyl)-5-methoxy-2-methyl-3-indoleacetoxy]-ethyl-N-3-(N-benzoyl-N',N'-di-n-propyl-DL-isoglutaminoyl)-oxypropyl-piperazine.

7. The composition of claim 5, in orally administrable form, containing 50–150 mg of the said active component.

8. The composition of claim 5 in suppository form, containing 100–200 mg of the said active component.

9. An anti-inflammatory, anti-rheumatic composition consisting essentially of a compound or salt of claim 2 and a pharmaceutically acceptable excipient.

10. An anti-inflammatory, anti-rheumatic composition consisting essentially of a salt of claim 4 and a pharmaceutically acceptable excipient.

* * * * *